United States Patent [19]

Miyagi et al.

[11] Patent Number: 5,740,965
[45] Date of Patent: Apr. 21, 1998

[54] ADHESIVE SPRAYER FOR LIVING BODY

[75] Inventors: Kunihiko Miyagi; Hidetoshi Yoshizawa, both of Tokyo, Japan

[73] Assignee: Machida Endoscope Co., Ltd., Tokyo, Japan

[21] Appl. No.: 634,630

[22] Filed: Apr. 18, 1996

[30] Foreign Application Priority Data

Apr. 18, 1995 [JP] Japan .................................. 7-115317
Jun. 21, 1995 [JP] Japan .................................. 7-178265

[51] Int. Cl.$^6$ .................................................. B05B 7/06
[52] U.S. Cl. ........................ 239/423; 239/428; 239/588; 604/82
[58] Field of Search ............................ 239/302, 303, 239/304, 306, 418, 422, 423, 424, 428, 587.1, 587.5, 588; 222/137, 145.1; 604/24, 82

[56] References Cited

U.S. PATENT DOCUMENTS

| 4,874,368 | 10/1989 | Miller et al. ............... 604/82 |
| 5,474,540 | 12/1995 | Miller et al. ............... 604/82 X |

FOREIGN PATENT DOCUMENTS

| A-0 156 098 | 12/1984 | European Pat. Off. |
| 0 449 294 | 9/1991 | European Pat. Off. |
| A-0 605 796 | 12/1993 | European Pat. Off. |
| A-0 534 140 | 1/1995 | European Pat. Off. |
| WO-A-90-13260 | 11/1990 | WIPO |
| WO-A-91-07197 | 5/1991 | WIPO |

OTHER PUBLICATIONS

Triple Lumen Spray Tube, Feb. 1994.

*Primary Examiner*—Andres Kashnikow
*Assistant Examiner*—Steven J. Ganey
*Attorney, Agent, or Firm*—Fish & Richardson P.C.

[57] ABSTRACT

In an adhesive sprayer for a living body, a hard insert portion extends from a sprayer body, a bendable portion extends from a distal end of the insert portion, and a nozzle portion is disposed on a distal end of this bendable portion. Gas from a gas inlet port formed in the sprayer body is injected from a gas injection port formed in the nozzle portion after passing through a passage which is allowed to extend through the interiors of the sprayer body, insert portion and bendable portion. Adhesive from an adhesive inlet port formed in the sprayer body is injected from an adhesive discharge port formed in the nozzle portion after passing through another passage which is allowed to extend through the interiors of the sprayer body, insert portion, and bending portion. The bending portion is bent by controlling a control member mounted on the sprayer body via a control cable extending through the interiors of the sprayer body, insert portion and bendable portion.

9 Claims, 8 Drawing Sheets

ADHESIVE SPRAYER FOR LIVING BODY

BACKGROUND OF THE INVENTION

This invention relates to a sprayer for spraying an adhesive towards a diseased part, such as an open wound, a trace of surgical excision or the like, of a living body such as a human body for the purpose of closing or covering the same.

An adhesive sprayer for a living body disclosed under the title of "TRIPLE LUMEN SPRAY TUBE" in a catalog distributed February 1994 is, in operation, inserted deep into a living body and then sprays an adhesive towards a diseased part in the living body. This type of an adhesive sprayer includes a sprayer body, a hard insert portion extending from the body, and a nozzle portion disposed on a distal end of the insert portion. The sprayer body has one gas inlet port and two adhesive inlet ports, whereas the nozzle portion has one gas injection port and two adhesive discharge ports. A pressurized gas from the gas inlet port is injected from the gas injection port after passing through a passage formed within the sprayer body and insert portion, and two kinds of adhesives from a syringe connected to the adhesive inlet ports are discharged from the adhesive discharge ports after passing through other passages formed in the spray body and insert portion, thereby spraying the adhesives towards the diseased part of the living body.

However, the hardness of the insert portion of the sprayer over an entire length thereof makes it difficult to bring the gas injection port and the adhesive discharge ports formed in the nozzle portion into an opposing relation with respect to the diseased part of a patient unless an organ of the patient is considerably moved and/or the patient is turned sideways, particularly when the diseased part, towards which the adhesives are to be sprayed, is located behind another organ or organs. For this reason, effort required for spraying the adhesives is increased and the patient is obliged to bear a heavy load.

SUMMARY OF THE INVENTION

It is, therefore, an object of the present invention to provide an adhesive sprayer for a living body in which a gas injection port and adhesive discharge ports can easily be placed opposite an diseased part a an adhesive spray work can correctly be performed in an efficient manner.

According to the present invention, there is provided an adhesive sprayer for a living body, the adhesive sprayer comprising:

(a) a sprayer body having an adhesive inlet port and gas inlet port;

(b) a hard insert portion extending from the sprayer body;

(c) a bendable portion extending from a distal end of the insert portion;

(d) a nozzle portion disposed on a distal end of the bendable portion, the nozzle portion including an adhesive discharge port and a gas injection port;

(e) first passage means for intercommunicating the adhesive inlet port of the sprayer body and the adhesive discharge port of the nozzle portion so that an adhesive is allowed to pass therethrough, the first passage means being disposed within the sprayer body, insert portion and bendable portion, the first passage means being bendable at least at the bendable portion;

(f) second passage means for intercommunicating the gas inlet port of the sprayer body and the gas injection port of the nozzle portion so that a pressurized gas is allowed to pass therethrough, the second passage means being disposed within the sprayer body, insert portion and bendable portion, the second passage means being bendable at least at the bendable portion; and (g) control means for remote controlling the bendable portion, the control means including a control member disposed on the sprayer body and at least one control cable, one end of the cable being secured to the control member and the other end thereof being secured to a distal end of the bendable portion.

DETAILED DESCRIPTION OF THE EMBODIMENT

A sprayer according to one embodiment of the present invention will now be described with reference to the accompanying drawings. This sprayer is of the type capable of spraying two kinds of liquid adhesives. These adhesives, when sprayed against a diseased part of a living body, are hardened by interaction thereof. These adhesives contain components capable of enhancing growth of the tissue of the living body.

Figure 1:
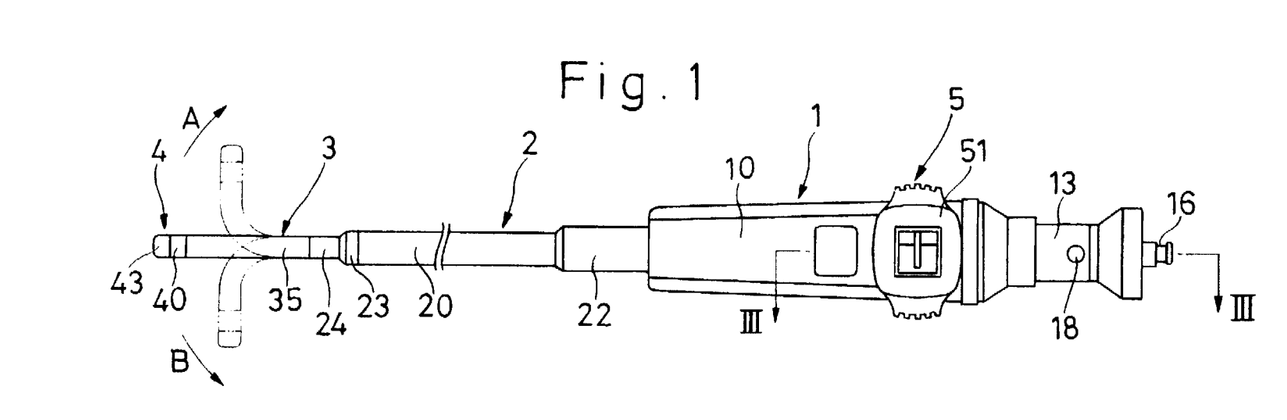
FIG. 1 is a plan view of a sprayer according to one embodiment of the present invention.
Figure 2:
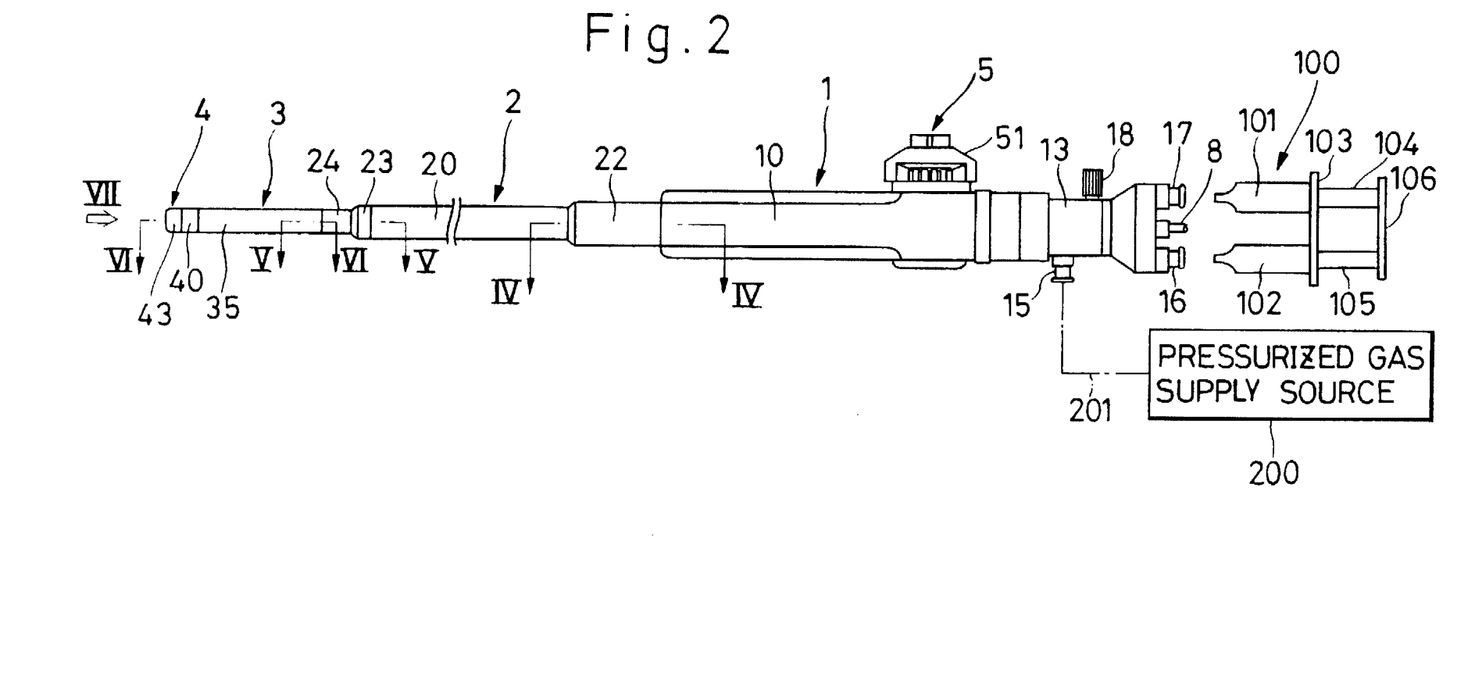
FIG. 2 is a side view of the above sprayer.

A general construction of a sprayer will now be described with reference to FIGS. 1 and 2. The sprayer includes a sprayer body 1, a hard insert portion 2 extending from the sprayer body 1, a bendable portion 3 extending from a distal end of the insert portion 2 and a nozzle portion 4 disposed on a distal end of the bendable portion 3.

Figure 3:
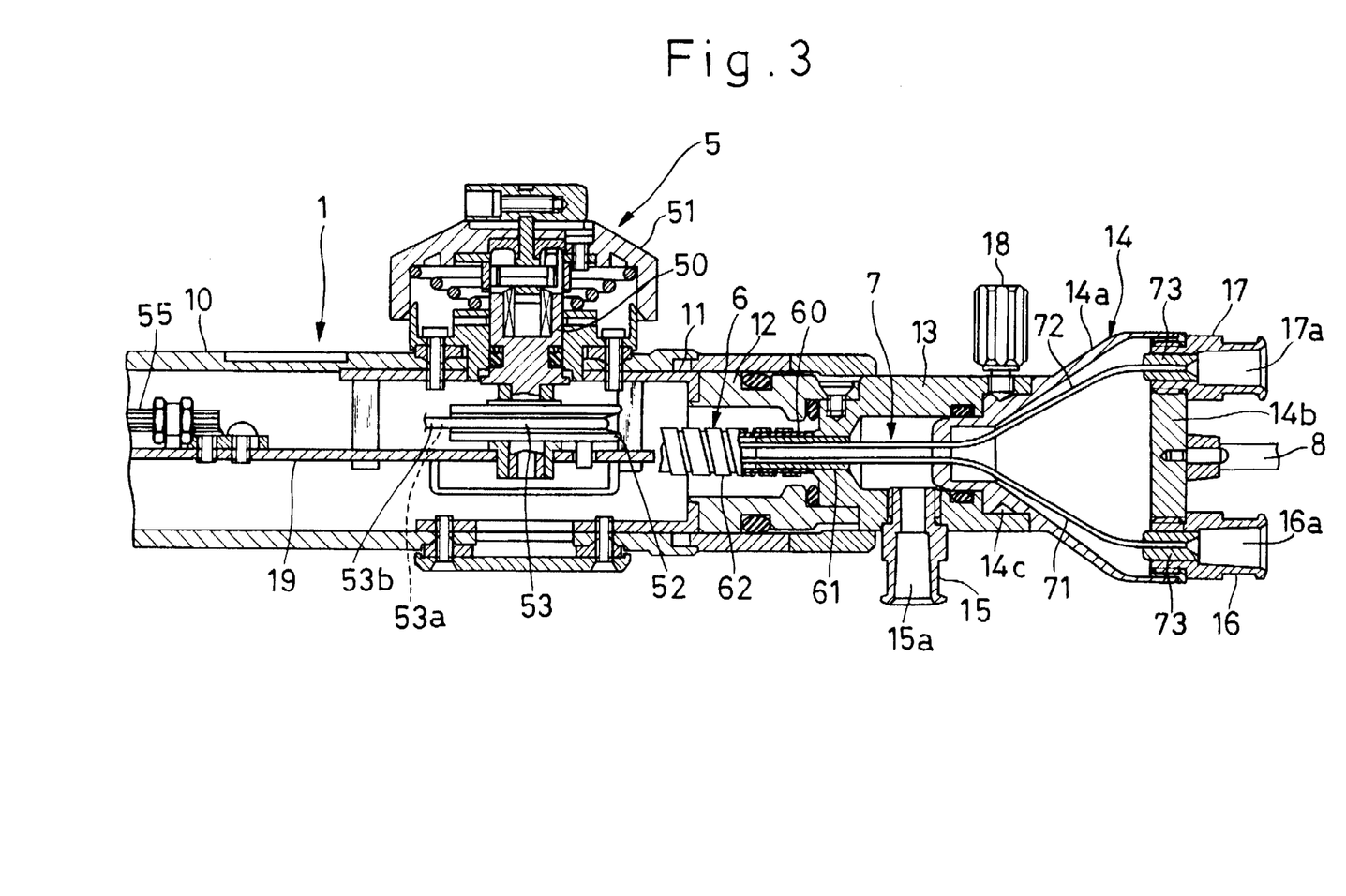
FIG. 3 is an enlarged sectional view taken on line III—III of FIG. 1.

As best shown in FIG. 3, the spray body 1 includes a hollow main sleeve 10 having a generally rectangular configuration in section, a connection member 11 received in and secured to the main sleeve 10, a cylindrical first auxil-

3 iary sleeve 12 secured to the connection member 11 and disposed on a rear end of the main sleeve 10, a cylindrical second auxiliary sleeve 13 secured to a rear end portion of the first auxiliary sleeve 12 and a holder 14 detachably connected to a rear end portion of the second auxiliary sleeve 13.

A mouthpiece 15 is attached to a peripheral wall of the second auxiliary sleeve 13. An inside passage 15a of the mouthpiece 15 is provided as a gas inlet port. The holder 14 includes a funnel member 14a whose diameter is enlarged backwardly and a closure 14b for closing an opening of the rear end of the funnel member 14a. Two mouthpieces 16 and 17 are attached to the closure 14b of the holder 14. Internal passages 16a and 17a of the mouthpieces 16 and 17 are provided as adhesive inlet ports, respectively.

An annular engagement groove 14c is formed in an outer periphery of a distal end portion of the funnel member 14a of the holder 14. With the distal end portion of the holder 14 inserted into the rear end portion of the second sleeve 13, a distal end portion of a stopper 18 threaded into a peripheral wall of the rear end portion of the second auxiliary sleeve 13 is brought into engagement in the engagement groove 14c. By doing this, the holder 14 is detachably connected to the second auxiliary sleeve 13.

A support plate 19 extending longitudinally of the main sleeve 10 is received in the main sleeve 10. This support plate 19 is secured to the main sleeve 10 through the connection member 11. The support plate 19 is adapted to support various component elements as later described.

Figure 4:
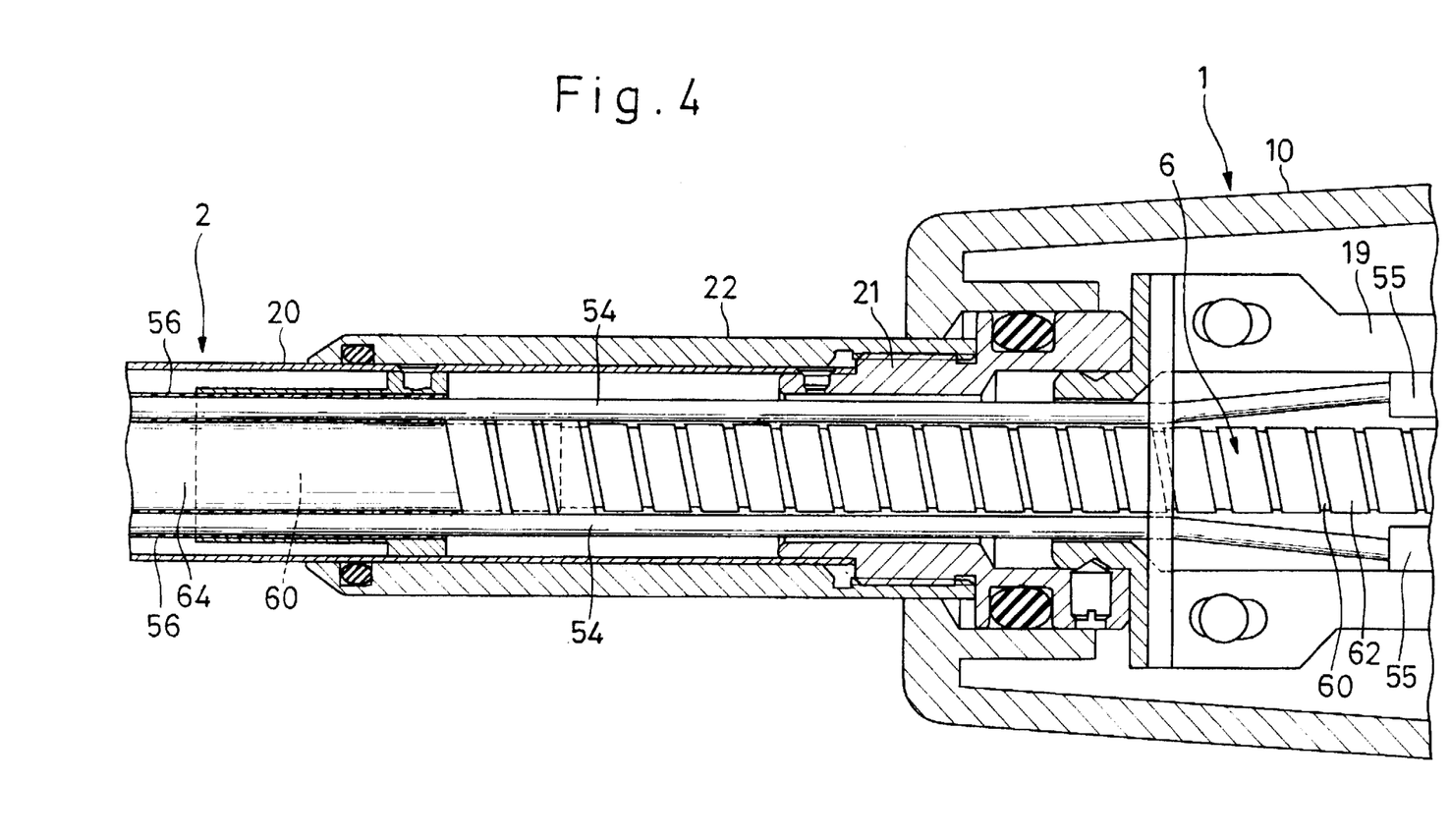
FIG. 4 is an enlarged sectional view taken on line IV—IV of FIG. 2.
Figure 5:
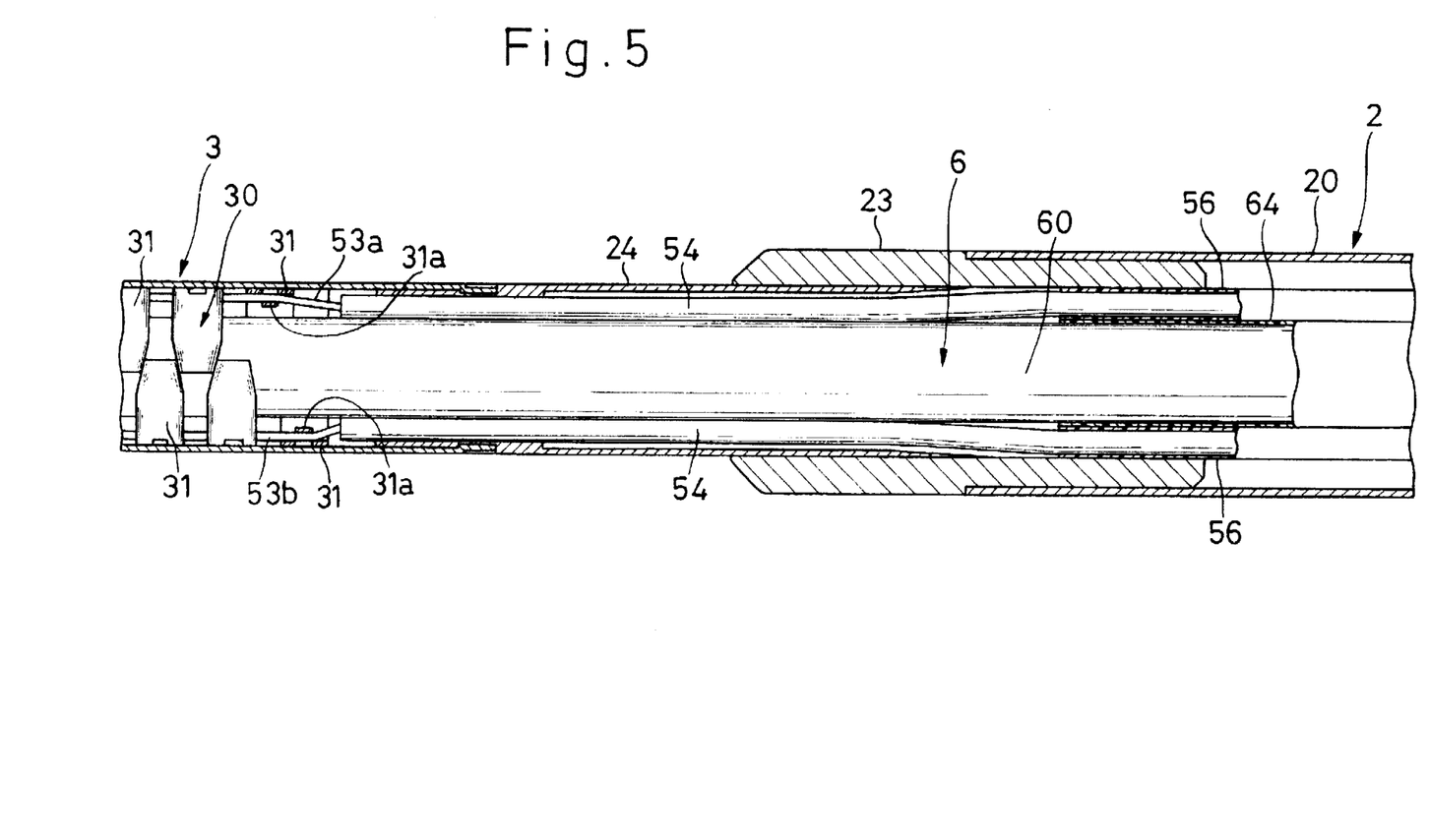
FIG. 5 is an enlarged sectional view taken on line V—V of FIG. 2.

The insert portion 2 includes a long metal pipe 20. As shown in FIG. 4, a rear end portion of the pipe 20 is secured to a distal end portion of the support plate 19 through the connection sleeve 21. The connection portion between the pipe 20 and the connection sleeve 21 is covered with a protective sleeve 22 which is threadedly fitted to the connection sleeve 21. As shown in FIG. 5, a distal end portion of the pipe 20 is connected to a thin connection sleeve 24 through a thick connection sleeve 23. The connection sleeve 24 is smaller in diameter than the pipe 20. The insert portion 2 comprises the pipe 20, and the connection sleeves 23 and 24.

Figure 6:
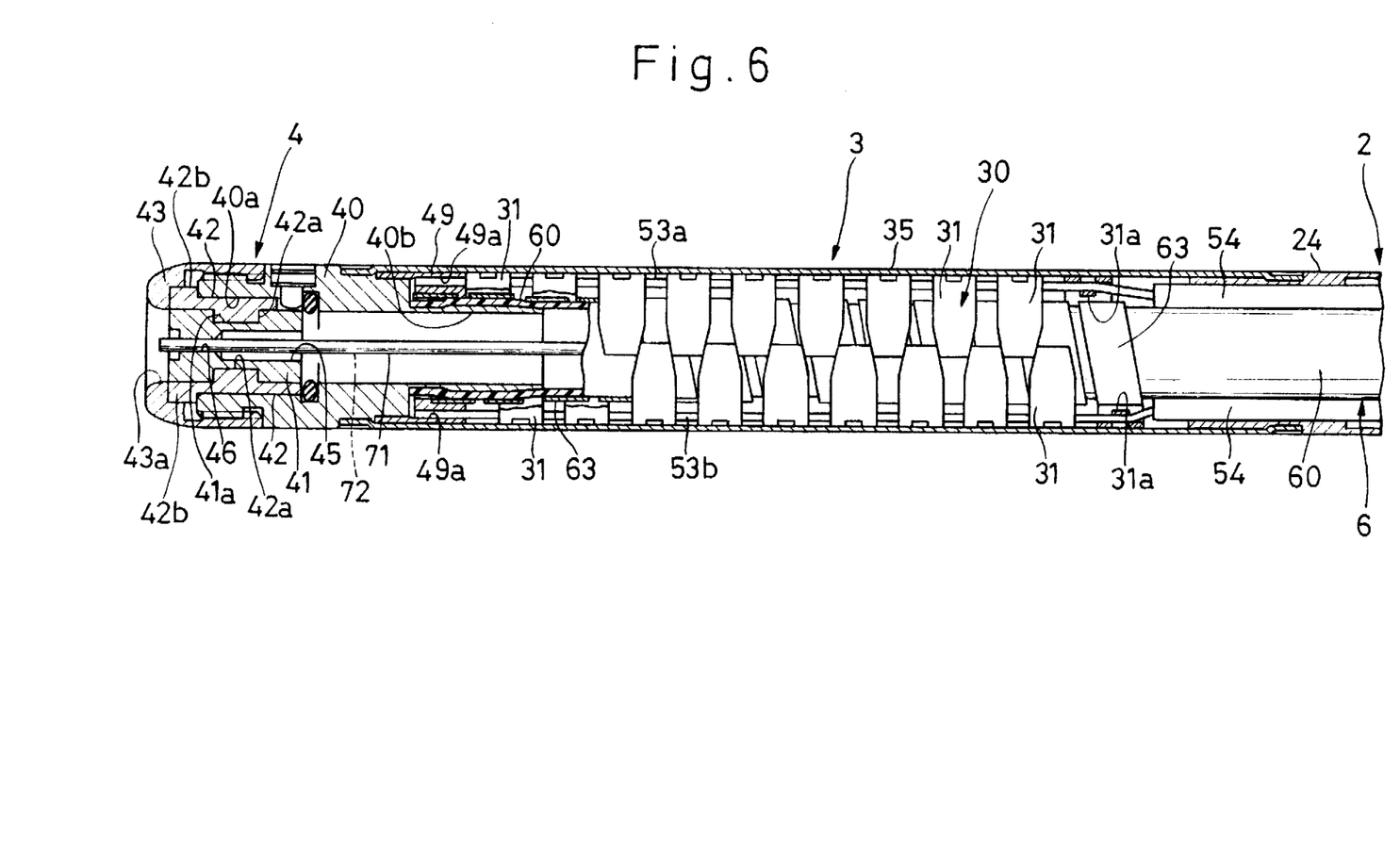
FIG. 6 is an enlarged sectional view taken on line VI—VI of FIG. 2.

As shown in FIG. 6, the bendable portion 3, which has a similar construction to that of a bendable portion of an endoscope, comprises an inside structure 30 and a protective tube 35 covering this inside structure 30. The inside structure 30 is constructed by turnably interconnecting a plurality of joints 31. More specifically, each joint 31 is constituted of a warped plate having a generally semi-arcuate configuration. Opposite end portions in the circumferential direction of the warped plate are rounded inwardly to define sleeve portions (not shown), respectively. A pair of connection wires (not shown) are allowed to pass respectively through those sleeve portions. Owing to this arrangement, one joint 31 is connected to adjacent joints such that those connected joints can be turned about the opposite end portions thereof. The protective tube 35 is constituted of a braid and a soft resin layer disposed on an outer periphery of the braid. The joint 31 at the rearmost end is connected to a distal end of the connection sleeve 24 of the insert portion 2, whereas a rear end portion of the protective tube 35 is secured to an outer periphery of the distal end portion of the connection sleeve 24 by means of spool and adhesive.

As shown in FIG. 6, the nozzle portion 4 includes an outer sleeve 40. The joint 31 at the foremost end of the bendable portion 3 is connected to a rear end of this outer sleeve 40 through a connection sleeve 49. Similarly, a distal end portion of the protective tube 35 goes beyond the connection sleeve 49 and is secured to an outer periphery of the rear end portion of the outer sleeve 40 by means of spool and adhesive.

As shown in FIG. 6, aside from the outer sleeve 40, the nozzle portion 4 includes an inner sleeve 41 received in the outer sleeve 40, a pair of clamping tips 42 for clamping the inner sleeve 41 within the outer sleeve 40, and a sleeve-like holding nut 43 for holding the pair of clamping tips 42 within the outer sleeve 40.

Figure 8:
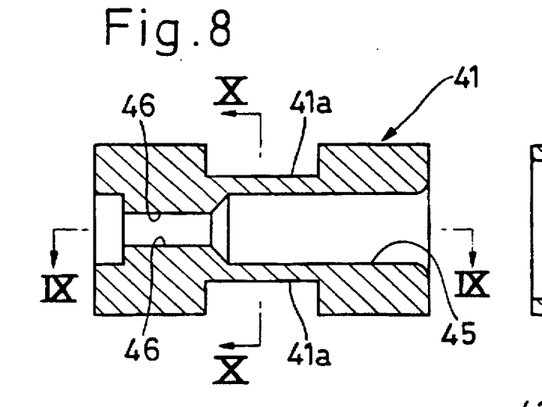
FIG. 8 is an enlarged sectional view of a nozzle member.
Figure 9:
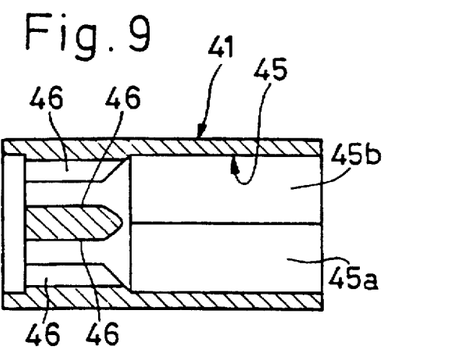
FIG. 9 is a sectional view taken on line IX—IX of FIG. 8.
Figure 10:
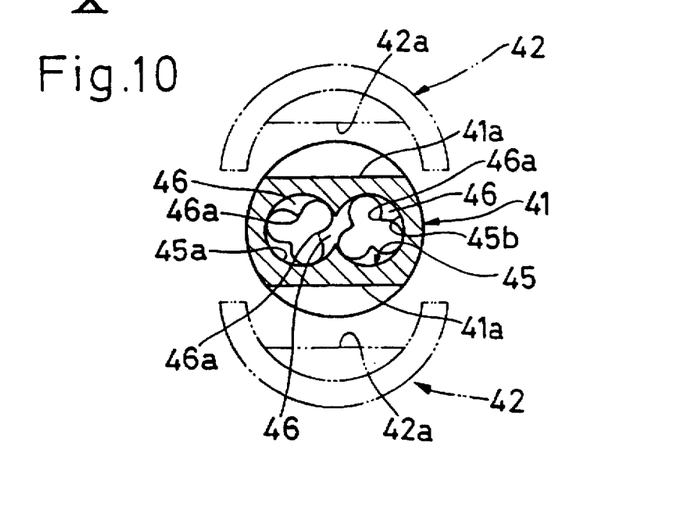
FIG. 10 is a sectional view taken along line X—X of FIG. 8.

Each component element of the nozzle portion 4 will now be described in detail. The outer sleeve 40 has a receiving space 40a of a circular configuration in cross section at its distal end portion. As shown in FIG. 10, each clamping tips 42 is of a semi-cylindrical configuration and has a projection 42a formed on an inner surface of a central portion in an axial direction thereof. As shown in FIGS. 8 through 10, a pair of recesses 41a are formed in an outer peripheral surface of a central portion in an axial direction of the inner sleeve 41. The pair of tips 42 are received in the receiving space 40a of the outer sleeve 40 with the projections 42a of the pair of clamping tips 42 fitted in the pair of recess portions 41a of the inner sleeve 41. In the foregoing state where the pair of tips 42 are received in the receiving space 40a, the holding nut 43 is threadedly engaged with the outer periphery of the distal end portion of the outer sleeve 40. By sandwiching a semi-arcuate flange portion 42b which is formed on the distal end portion of each clamping tip 42 between an annular flange portion 43a of the holding nut 43 and a distal end face of the outer sleeve 40, the clamping tips 42 are supported by the outer sleeve 40 and thus the inner sleeve 41 is supported by the outer sleeve 40.

As shown in FIGS. 6 through 10, a passage extending axially of the sleeve 41 is provided as a gas injection port 45. This gas injection port 45 is of the type in which two passage portions 45a and 45b each having a circular configuration in section are integrally jointed. The sectional configuration of the port 45 resembles a numerical FIG. "8". Three projections 46 are circumferentially equally spacedly formed on an inner peripheral surface in an area in the vicinity of the distal end portion of the gas injection port 45 for every passage portion 45a, 45b. These projections 46 are allowed to extend in the axial direction and each has a chevron configuration in section. Ridge lines 46a of the chevron-shaped projections 46 are provided respectively as support portions for tubes 71 and 72 as later described.

A control means for remote controlling the bendable portion 3 will be described next. This remote control means 5 includes a shaft 50 extending through a wall of the sprayer body 1, a control knob 51 attached to one end of the shaft 50 outside the sprayer body 1, a pulley 52 attached to the other end of the shaft 51 inside the sprayer body 1, and a cable 53. This cable 53 is wound at a central portion thereof around the pulley 52 over a half circumference of the pulley 52, and firmly secured at one point to the pulley 52. The cable 53 has two portions extending forwardly from the pulley 52. These two portions of the cable 53 are hereinafter referred to as control cables 53a and 53b.

As shown in FIGS. 4 through 6, the control cables 53a and 53b are pierced respectively into two guide tubes 54 extending over the sprayer body 1 and the insert portion 2. The guide tubes 54 are each formed by spirally winding a metal wire, and rear ends of the guide tubes 54 are fixedly inserted respectively into support tubes 55 (FIGS. 3 and 4) which are secured respectively to support plates 19 within the sprayer body 1. The guide tubes 54 are arranged in opposing relation with each other in a radial direction of the insert portion 2. As shown in FIGS. 5 and 6, distal end portions of the guide tubes 54 are secured to a distal end of the connection sleeve 24. Each guide tube 54 is covered with a protective tube 56 made of resin at the insert portion 2.

As shown in FIGS. 5 and 6, the control cables 53a and 53b further extend forwardly beyond the distal ends of the guide tubes 54. After passing through the bendable portion 3, the distal ends of the control cables 53a and 53b are fixedly inserted into a pair of fixing holes 49a formed in the connection sleeve 49 of the nozzle portion 4 in radially opposing relation with each other. A guide portion 31a is formed on a central portion in the circumferential direction of the joint 31 of the bendable portion 3. This guide portion 31a is formed by cut-and-raise treatment (or upwardly press working treatment). The control cables 53a and 53b are pierced into the guide portions 31a of every other joints 31 so that the cables 53a and 53b are arranged in radially opposing relation with each other.

Next, a passage means 6 to supply gas therethrough will be described. This passage means 6 includes a flexible tube 60 made of resin. The tube 60 extends from the sprayer body 1 up to the nozzle portion 4 via the insert portion 2 and the bendable portion 3. As shown in FIG. 3, a rear end portion of the tube 60 is secured to a distal end portion of the second auxiliary sleeve 13 of the sprayer body 1. As shown in FIG. 6, a distal end portion of the tube 60 is secured to an outer periphery of a sleeve-like connection portion 40b having a reduced diameter. This sleeve-like connection portion 40b is formed on the rear end portion of the outer sleeve 40 of the nozzle portion 4. The passage means 6 comprises this tube 60, the second auxiliary sleeve 13, a joint tube 61 and the outer sleeve 40, and the hollow interiors of those component members serve to interconnect the gas inlet port 15a of the mouthpiece 15 of the sprayer body 1 and the gas injection port 45 of the inner sleeve 41 of the nozzle portion 4.

As shown in FIGS. 3 and 4, the tube 60 is covered with a protective tube 62 which is constructed by spirally winding a thin strip metal sheet within the sprayer body 1, so that the tube 60 will not be scarred by direct contact with movable component elements of the sprayer body 1. Similarly, as shown in FIG. 6, the tube 60 is covered with a protective tube 63 which is constructed by spirally winding a thin strip metal sheet within the bendable portion 3, so that the tube 60 will not be scarred by direct contact with the joints 31. Further, as shown in FIGS. 4 and 5, the tube 60 is covered with a thin protective tube 64 made of resin at the insert portion 2.

Figure 7:
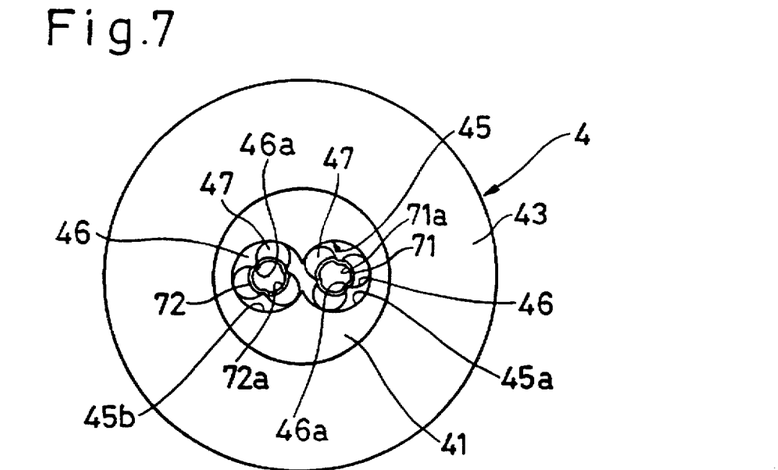
FIG. 7 is an enlarged view of a distal end face of the sprayer when viewed in a direction as indicated by an arrow VII.

Next, the passage means 7 for supplying adhesive will be described. This passage means 7 includes a pair of flexible tubes 71 and 72 which are made of resin. These tubes 71 and 72 are considerably narrow compared with the tube 60 and extend from the sprayer body 1 up to the nozzle portion 4 via the insert portion 2 and the bendable portion 3. As shown in FIG. 3, rear end portions of the tubes 71 and 72 are fixedly inserted into the distal end portions of the mouthpieces 16 and 17 of the sprayer body 1 through a joint sleeve 73. The tubes 71 and 72 extend through the interiors of the holder 14, the second auxiliary sleeve 13, the tube 60 and the outer sleeve 40 of the nozzle portion 4. As shown in FIGS. 6 and 7, distal end portions of the tubes 71 and 72 are press fitted into a space between the projections 46 which are formed respectively on the two passage portions 45a and 45b of the gas injection port 45 of the inner sleeve 41. In that state, the tubes 71 and 72 are, as shown in FIG. 7, elastically deformed and the ridge lines 46a of the projections 46 support the tubes 71 and 72.

Distal end openings of the tubes 71 and 72 are provided respectively as adhesive discharge ports 71a and 72a. These tubes 71 and 72 interconnect the adhesive inlet ports 16a and 17a and the adhesive discharge ports 71a and 72a, respectively.

As described above, the sprayer body 1, the insert portion 2, the bendable portion 3 and the nozzle portion 4 have hollow interiors, respectively. These hollow interiors are continuous with each other, and held air-tight using 0-rings or the like, excepting the ports 15a and 45.

A sprayer thus constructed is used, for example, for covering the wound of a patient's lung whose body is surgically cut open or for covering a part of the patient's body from where a cancerous knob has been removed. As shown in FIG. 2, a syringe 100 is preliminarily attached to the sprayer body 1. The syringe 100 includes two cylinders 101 and 102, a plate 103 secured to rear ends of the cylinders 101 and 102, two pistons 104 and 105 distal end portions of which are inserted respectively into the cylinders 101 and 102, and another plate 106 secured to rear ends of the pistons 104 and 105. Adhesives containing different components are stored in the cylinders 101 and 102, respectively. With the distal end portions of the cylinders 101 and 102 inserted respectively into the mouthpieces 16 and 17, the plate 103 is secured to the sprayer body 1 by a fixing device 8 (only a part of it is shown) disposed on the rear end portion of the sprayer body 1. A distal end of a tube 201 extending from a pressurized gas supply source 200 is connected to the mouthpiece 15. As the pressurized gas such as, inert nitrogen gas is used.

In operation, the sergeant holds the sprayer body 1 with one hand and inserts the insert portion 2 into the body of the patient until the nozzle portion 4 comes closer to the diseased part. Since the insert portion 2 is hard, it can positively be brought closer to the diseased part without any worry about the insert port 2 being bent by organs. At that time, in case the diseased part is located away from an extension of an axis of the insert portion 2, the control knob 51 is turned to bend the bendable portion 3. More specifically, when the control knob 51 is turned clockwise in FIG. 1, the control cable 53a is pulled and the other control cable 53b is loosened. Accordingly, the bendable portion 3 is bent in an A-direction. When the control knob 51 is turned counterclockwise, the control cable 53b is pulled and the other control cable 53a is loosened this time. Accordingly, the bendable portion 3b is bent in a B-direction. A bending amount of the bendable portion 3 corresponds to a turning amount of the control knob 51. In this way, by bending the bendable portion 3, the gas injection port 45 and the adhesive discharge ports 71a and 72a of the nozzle portion 4 can be placed opposite the diseased part, thus enabling to easily and correctly perform a spraying operation of adhesives as later described. Further, since the organ of the patient is not required to be moved considerably, and since the patient's body is not required to be turned sideways, a load to the patient is reduced.

Then, in the state that the nozzle portion 4 is placed opposite the diseased part as mentioned above, a pressurized gas from the pressurized gas supply source 200 is supplied to the diseased part from the gas injection port 45 of the nozzle portion 4 via the passage means 6 including the tube 201, the gas inlet port 15a of the sprayer body 1 and the tube 60. While the gas injection is undergoing, the sergeant pushes the plate 106 of the syringe 100 towards the plate 103. By doing this, the pistons 104 and 105 are moved forwardly to extrude or push out the adhesives within the cylinders 101 and 102. The adhesives thus pushed out are delivered from the adhesive inlet ports 16a and 17a towards the distal ends of the tubes 71 and 72 and then discharged from the adhesive discharge ports 71a and 72a. The discharged adhesives are atomized by the discharged pressurized gas, admixed and then sprayed towards the diseased part. The adhesives, which have been sprayed to the diseased part, are hardened thereby enabling to close or cover the diseased part.

Since the pressurized gas is injected from the periphery of the adhesive discharge ports 71a and 72a, i.e., from three gaps 47 (FIG. 7) defined by the outer peripheral surfaces of the distal end portions of the tubes 71 and 72 and the inner peripheral surface of the gas injection port 45, the adhesives can uniformly favorably atomized and the spraying direction of the adhesive agents can be brought into alignment with the axis of the nozzle portion 4. Thus, the adhesives can correctly be directed towards the diseased part.

Incidentally, it sometimes happens that when a sprayer is used for a long time, the adhesive discharge ports 71a and 72a are gradually closed by the adhesives, an injection amount of adhesives becomes short or the adhesives are so greatly reduced in amount that it cannot be discharged at all. In such a case, the tubes 71 and 72, the inner sleeve 40 of the nozzle portion 4 and the holder 14 of the sprayer body 1 are removed so as to be replaced by new ones, respectively.

More specifically, the holding nut 43 is removed from the outer sleeve 40. Then, the clamping tip 42 and the inner sleeve 41 are withdrawn forwardly from the outer sleeve 40. At that time, it is preferred that the tubes 71 and 72 are received in their slightly released states so that the clamping tips 42 and the inner sleeve 41 can easily be withdrawn forwardly. Thereafter, the distal end portions of the tubes 71 and 72 are withdrawn from the inner sleeve 41 or the tubes 71 and 72 are cut off at areas in the vicinity of the inner sleeve 41. Then, the stopper 18 of the sprayer body 1 is loosened in order to remove the engagement between the stopper 18 and the holder 14. Thereafter, the holder 14 is withdrawn from the second auxiliary sleeve 13 and the holder 14 is further moved backwardly in order to remove the tubes 71 and 72 from the tube 60 and the sprayer body 1. Thus removed inner sleeve 41, the tubes 71 and 72 and the holder 14 are discarded. The inner sleeve 41 and the holder 14 may be reused. Then, a new holder 14, new tubes 71 and 72 whose rear ends are connected to the holder 14 and a new inner sleeve 41 are prepared. The new tubes 71 and 72 are pierced into the tube 60 from the rear end opening portion of the sprayer body 1 and distal end portions of the new tubes 71 and 72 are allowed to project from the outer sleeve 40. Then, the distal end portions of the tubes 71 and 72 are press fitted into the new inner sleeve 41. Thereafter, the inner sleeve 41 is attached to the outer sleeve 40 by the clamping tips 42 and the holding nut 43. Then, the holder 14 is detachably attached to the second auxiliary sleeve 13 using the stopper 18.

Figure 11:
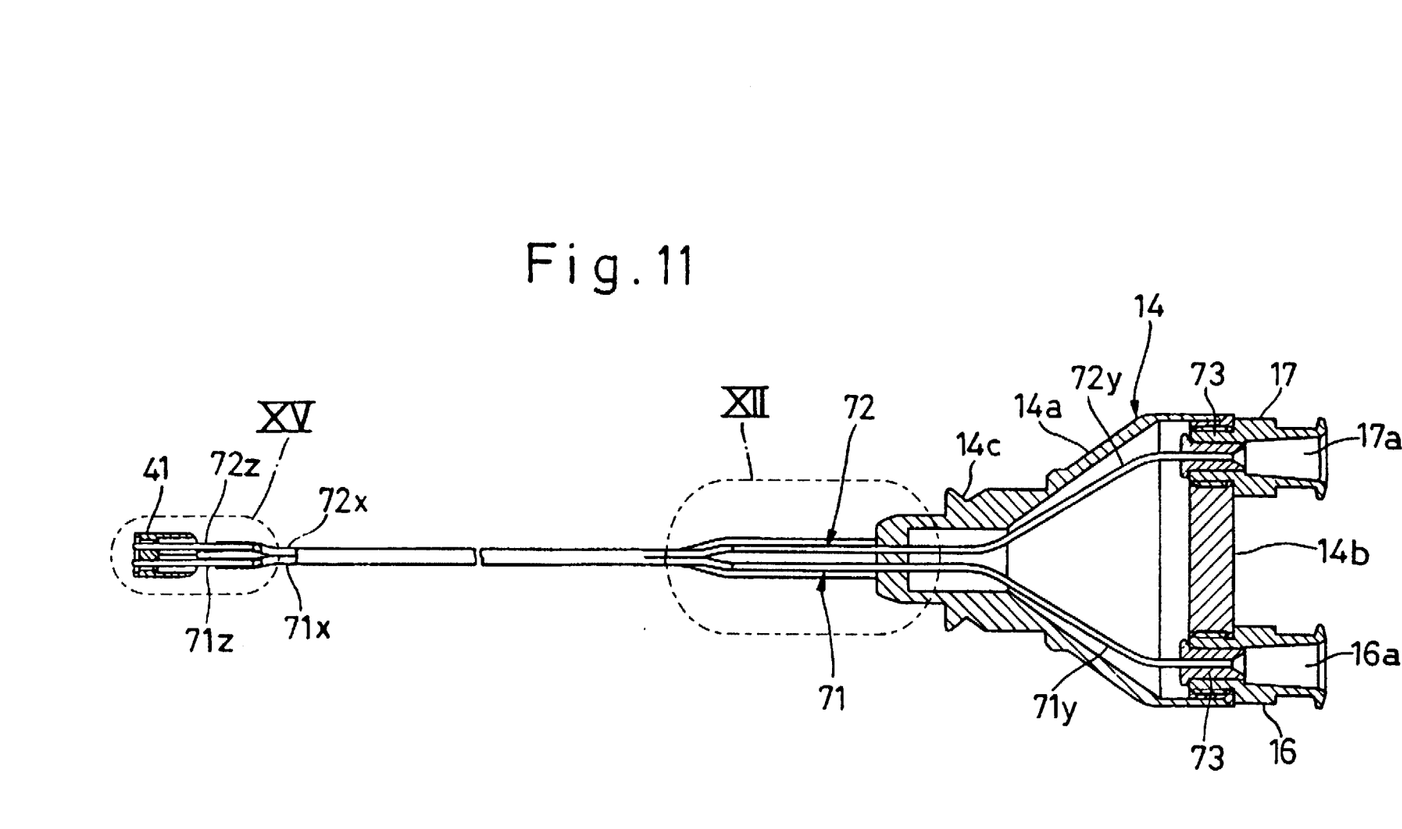
FIG. 11 is a sectional view showing an exchangeable cartridge according to another embodiment of the present invention.
Figure 12:
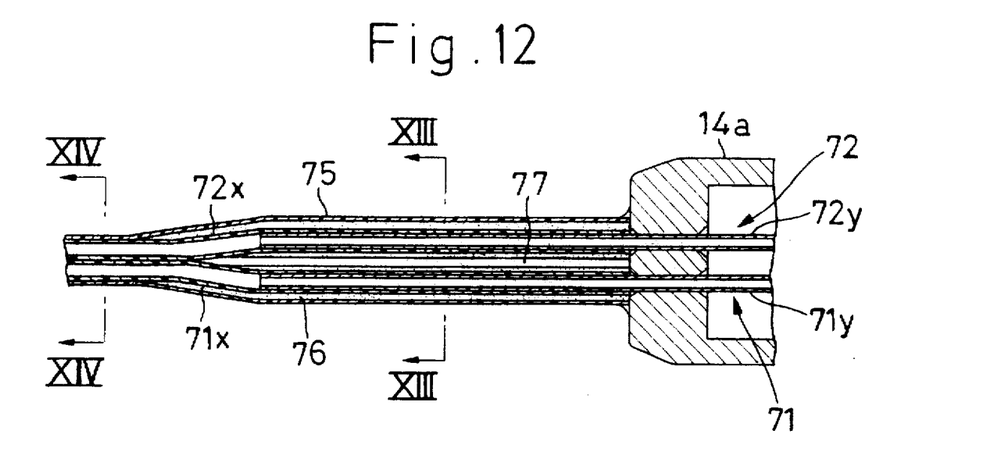
FIG. 12 is an enlarged sectional view of an XII-portion of FIG. 11.
Figure 13:
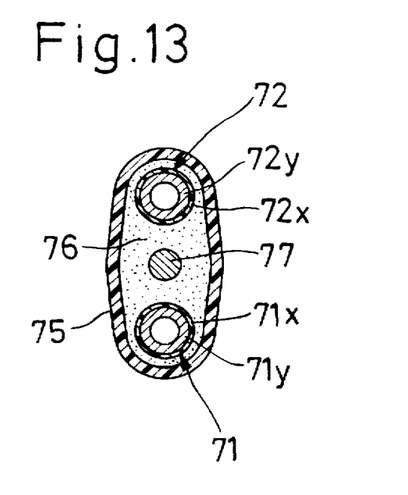
FIG. 13 is a sectional view taken on line XIII—XIII of FIG. 12.
Figure 14:
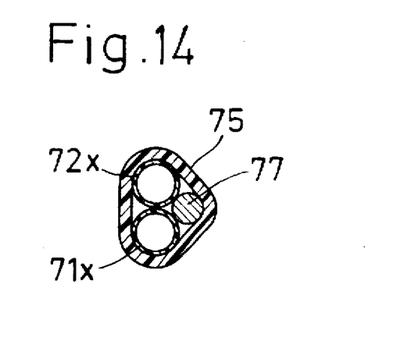
FIG. 14 is a sectional view taken on line XIV—XIV of FIG. 12.
Figure 15:
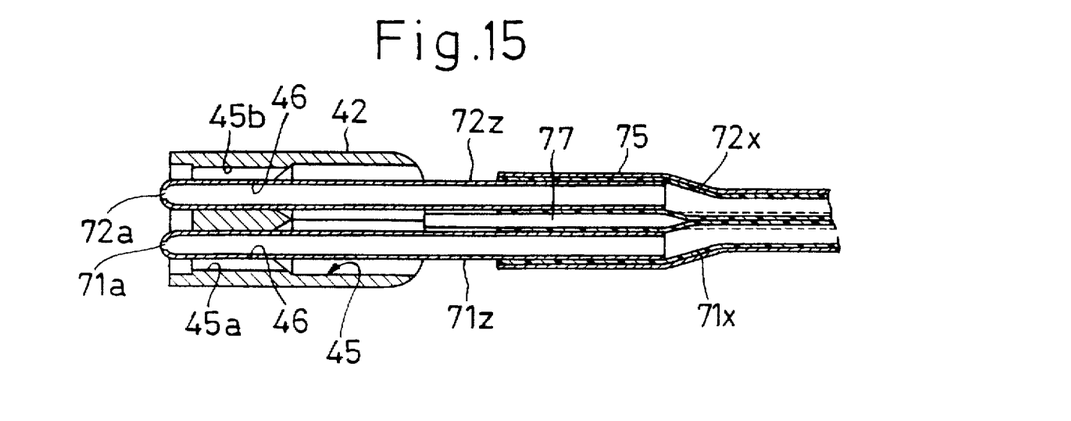
FIG. 15 is an enlarged sectional view of an XV-portion of FIG. 11.

FIGS. 11 through 15 show another embodiment. In this embodiment, component parts corresponding to those of the first embodiment are denoted by same reference numerals, and description thereof is omitted. In this embodiment, as shown in FIG. 11, tubes 71 and 72 for allowing passage of adhesive, a holder 14 and an inner sleeve 41 are integrally formed to thereby constitute an exchangeable cartridge. The tubes 71 and 72 respectively include flexible resin tubes 71x and 72x, metal tubes 71y and 72y connected respectively to rear ends of the resin tubes 71x and 72x, and metal tubes 71z and 72z connected respectively to distal ends of the resin tubes 71x and 72x. Distal end portions of the metal tubes 71y and 72y are allowed to extend through a distal end wall of the holder 14, whereas rear end portions thereof are secured respectively to the mouthpieces 16 and 17. Distal end portions of the metal tubes 71z and 72z are inserted into a gas injection port 45 of the inner sleeve 41 and secured respectively to ridge lines of projections 46 by welding or the like. Distal end openings of the metal tubes 71z and 72z are provided in the form of adhesive discharge ports 71a and 72a, respectively.

The inner sleeve 42 is the same in construction as the first embodiment. The inner sleeve 41 is supported on an outer sleeve 40 by a pair of clamping tips 41 and retainer nuts 43 (see FIG. 6). This embodiment is different from the first embodiment only in the respect that an outside diameter of the inner sleeve 41 is smaller than an inside diameter of an connection portion 40b of the outer sleeve 40 and therefore, the inner sleeve 41 can go all the way through the outer sleeve 40 and extend backwardly of the outer sleeve 40.

The cartridge has a metal reinforcing wire 77. This reinforcing wire 77 extends along the resin tubes 71x and 72x. A rear end portion of the reinforcing wire 77 is secured to a distal end portion of the holder 14 by hard resin 76, together with rear end portions of the resin tubes 71x and 72x and the distal end portions of the metal tubes 71y and 72y. A distal end of the reinforcing wire 77 is fixedly inserted in a fixed hole (not shown) formed in an rear end face of the inner sleeve 42. The reinforcing wire 77, the resin tubes 71x and 72x are covered with a protective tube 75.

For exchanging the cartridge, the inner sleeve 41 and the outer sleeve 40 are disengaged from each other and the holder 14 and the main sleeve 10 are disengaged from each other in the same manner as mentioned, and thereafter, the cartridge is drawn back as it is. A new cartridge for replacement is inserted for setting through a rear end opening of the main sleeve 10.

The present invention is not limited to the above embodiment but many changes can be made.

For example, it may be arranged such that when the holder 14 is disengaged from the stopper 18, the holder 14 can move a predetermined distance forwardly from the engaging position. Owing to this arrangement, the inner sleeve 41 can easily be withdrawn without loosening the tubes 71 and 72.

Further, the tubes 60, 71 and 72 may be bendable only at portions corresponding to the bendable portion 3.

The number of the projections 46 formed on the passage portions 45a, 45a of the inner sleeve 41 of the nozzle portion 4 may be four or more.

The pressurized gas supplying tube 60 may be eliminated. If eliminated, the hollow interiors of the sprayer body 1, the insert portion 2 and the bendable portion 3 serve as a passage for the pressurized gas.

The adhesive discharge port may be situated away from the gas injection port in the radial direction of the nozzle portion.

It may be arranged such that the sprayer sprays only one kind of adhesive. In that case, only one adhesive inlet port and only one adhesive discharge port may be provided.

The number of the control cable may be one. If only one cable is employed, the bendable portion is bent only in one direction. The number of the control cables may be four. In that case, the additional two control cables are associated with two control members each of which includes the shaft, the control knob and the pulley.

What is claimed is:

1. An adhesive sprayer for a living body, said adhesive sprayer comprising:

(a) a sprayer body having an adhesive inlet port and a gas inlet port;

(b) a hard insert portion extending from said sprayer body;

(c) a bendable portion extending from a distal end of said insert portion;

(d) a nozzle portion disposed on a distal end of said bendable portion, said nozzle portion including an adhesive discharge port and a gas injection port;

(e) first passage means for intercommunicating said adhesive inlet port of said sprayer body and said adhesive discharge port of said nozzle portion so that an adhesive is (d) a nozzle portion disposed on a distal end of the bendable portion, the nozzle portion including an adhesive discharge port and a gas injection port;

(e) first passage means for intercommunicating the adhesive inlet port of the sprayer body and the adhesive discharge port of the nozzle portion so that an adhesive is allowed to pass therethrough, the first passage means being disposed within the sprayer body, hard insert portion and bendable portion, the first passage means being bendable at least at the bendable portion;

(f) second passage means for intercommunicating the gas inlet port of said sprayer body and the gas injection port of the nozzle portion so that a pressurized gas is allowed to pass therethrough, the second passage means being disposed within the sprayer body, hard insert portion and bendable portion, said second passage means being bendable at least at the bendable portion;

(g) control means for remote controlling the bendable portion, the control means including a control member disposed on the sprayer body and at least one control cable, one end of the cable being secured to the control member and the other end thereof being secured to a distal end of the bendable portion;

wherein the first passage means has a first tube, the first tube being connected at a rear end thereof to the adhesive inlet port and inserted at a distal end portion thereof into the gas injection port formed in the nozzle portion, a gap for allowing allowed to pass therethrough, said first passage means being disposed within said sprayer body, insert portion and bendable portion, said first passage means being bendable at least at said bendable portion;

(f) second passage means for intercommunicating said gas inlet port of said sprayer body and said gas injection port of said nozzle portion so that a pressurized gas is allowed to pass therethrough, said second passage means including a separate flexible tube and being disposed within said sprayer body, insert portion and bendable portion, said second passage means being bendable at least at said bendable portion; and (g) control means for remote controlling said bendable portion, said control means including a control member disposed on said sprayer body and at least one control cable, one end of said cable being secured to said control member and the other end thereof being secured to a distal end of said bendable portion.

2. An adhesive sprayer according to claim 1, in which said control member includes a shaft extending through a wall of said sprayer body, a control knob mounted on an external end of said shaft and a pulley mounted on an internal end of said shaft, said control cable being secured to a peripheral surface of said pulley.

3. An adhesive sprayer according to claim 1, in which said first passage means has a first tube, said first tube being connected at a rear end thereof to said adhesive inlet port and inserted at a distal end portion thereof into said gas injection port formed in said nozzle portion, a gap for allowing supply of the pressurized gas being formed between an inner peripheral surface of said gas injection port and an outer peripheral surface of the distal end portion of said first tube, an opening of the distal end portion of said first tube being provided as said adhesive discharge port.

4. An adhesive sprayer according to claim 3, in which said gas injection port has three or more projections circumferentially spacedly formed in the inner peripheral surface of said gas injection port, the distal end portion of said first tube being press fitted among said projections in an elastically deformed fashion.

5. An adhesive sprayer according to claim 3, in which two of said adhesive inlet ports are formed in said sprayer body and two of said adhesive discharge ports are formed in said nozzle portion, said first passage means including two of said first tubes.

6. An adhesive sprayer for a living body, said adhesive sprayer comprising:

(a) a sprayer body having an adhesive inlet port and a gas inlet port;

(b) a hard insert portion extending from the sprayer body;

(c) a bendable portion extending from a distal end of the hard insert portion; supply of the pressurized gas being formed between an inner peripheral surface of the gas injection port and an outer peripheral surface of the distal end portion of the first tube, an opening of the distal end portion of the first tube being provided as the adhesive discharge port; and wherein said second passage means has a flexible second tube, a rear end of said second tube being continuous with said gas inlet port, a distal end of said second tube being connected to said nozzle portion and continuous with said gas injection port, said first tube being inserted into and extending through the interior of said second tube.

7. An adhesive sprayer for a living body, said adhesive sprayer comprising:

(a) a sprayer body having an adhesive inlet port and a gas inlet port;

(b) a hard insert portion extending from the sprayer body;

(c) a bendable portion extending from a distal end of the hard insert portion;

(d) a nozzle portion disposed on a distal end of the bendable portion, the nozzle portion including an adhesive discharge port and a gas injection port;

(e) first passage means for intercommunicating the adhesive inlet port of the sprayer body and the adhesive discharge port of the nozzle portion so that an adhesive is allowed to pass therethrough, the first passage means being disposed within the sprayer body, hard insert portion and bendable portion, the first passage means being bendable at least at the bendable portion;

(f) second passage means for intercommunicating the gas inlet port of said sprayer body and the gas injection port of the nozzle portion so that a pressurized gas is allowed to pass therethrough, the second passage means being disposed within the sprayer body, hard insert portion and bendable portion, said second passage means being bendable at least at the bendable portion;

(g) control means for remote controlling the bendable portion, the control means including a control member disposed on the sprayer body and at least one control cable, one end of the cable being secured to the control member and the other end thereof being secured to a distal end of the bendable portion;

wherein the first passage means has a first tube, the first tube being connected at a rear end thereof to the adhesive inlet port and inserted at a distal end portion thereof into the gas injection port formed in the nozzle portion, a gap for allowing supply of the pressurized gas being formed between an inner peripheral surface of the gas injection port and an outer peripheral surface of the distal end portion of the first tube, an opening of the distal end portion of the first tube being provided as the adhesive discharge port; and wherein said sprayer body includes a main sleeve and a holder detachably connected to said main sleeve, said holder being provided with said adhesive inlet port, the rear end of said first tube being connected to said holder, said nozzle portion including an outer sleeve and an inner sleeve withdrawably received in said outer sleeve, said gas injection port being formed in said inner sleeve.

8. An adhesive sprayer according to claim 7, in which said inner sleeve has such an outer diameter that said inner sleeve can be drawn backwardly of the rear end of said outer sleeve, and said first tube is secured to said inner sleeve, an exchangeable cartridge being constituted by said inner sleeve, first tube and holder.

9. An adhesive sprayer according to claim 8, in which said holder and said inner sleeve are connected with each other through a reinforcing wire, said reinforcing wire extending along said first tube.

* * * * *

UNITED STATES PATENT AND TRADEMARK OFFICE
CERTIFICATE OF CORRECTION

PATENT NO. : 5,740,965
DATED : April 21, 1998
INVENTOR(S) : Miyagi et al.

It is certified that error appears in the above-identified patent and that said Letters Patent is hereby corrected as shown below:

In the Claims:

In Claim 6, delete lines 3-12, and insert the following:

--(a) a sprayer body having an adhesive inlet port and a gas inlet port;

(b) a hard insert portion extending from the sprayer body;

(c) a bendable portion extending from a distal end of the hard insert portion;

(d) a nozzle portion disposed on a distal end of the bendable portion, the nozzle portion including an adhesive discharge port and a gas injection port;

(e) first passage means for intercommunicating the adhesive inlet port of the sprayer body and the adhesive discharge port of the nozzle portion so that an adhesive is allowed to pass therethrough, the first passage means being disposed within the sprayer body, hard insert portion and bendable portion, the first passage means being bendable at least at the bendable portion;

UNITED STATES PATENT AND TRADEMARK OFFICE
CERTIFICATE OF CORRECTION

PATENT NO. : 5,740,965
DATED : April 21, 1998
INVENTOR(S) : Miyagi et al.

It is certified that error appears in the above-identified patent and that said Letters Patent is hereby corrected as shown below:

<u>Claim 6, cont'd</u>

(f) second passage means for intercommunicating the gas inlet port of said sprayer body and the gas injection port of the nozzle portion so that a pressurized gas is allowed to pass therethrough, the second passage means being disposed within the sprayer body, hard insert portion and bendable portion, said second passage means being bendable at least at the bendable portion;

(g) control means for remote controlling the bendable portion, the control means including a control member disposed on the sprayer body and at least one control cable, one end of the cable being secured to the control member and the other end thereof being secured to a distal end of the bendable portion;

UNITED STATES PATENT AND TRADEMARK OFFICE
CERTIFICATE OF CORRECTION

PATENT NO. : 5,740,965
DATED : April 21, 1998
INVENTOR(S) : Miyagi et al.

It is certified that error appears in the above-identified patent and that said Letters Patent is hereby corrected as shown below:

wherein the first passage means has a first tube, the first tube being connected at a rear end thereof to the adhesive inlet port and inserted at a distal end portion thereof into the gas injection port formed in the nozzle portion, a gap for allowing supply of the pressurized gas being formed between an inner peripheral surface of the gas injection port and an outer peripheral surface of the distal end portion of the first tube, an opening of the distal end portion of the first tube being provided as the adhesive discharge port; and--

Signed and Sealed this

Twenty-third Day of March, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO.    : 5,740,965
DATED         : April 21, 1998
INVENTOR(S)   : Miyagi et al It is certified that error appears in the above-identified patent and that said Letters Patent is hereby corrected as shown below:

IN THE CLAIMS:

In Claim 1, delete lines 14-51 as they are duplicative of claim elements (d), (e), (f), and (g)--

Signed and Sealed this

Twenty-seventh Day of July, 1999

*Attest:*

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO. : 5,740,965
DATED : April 21, 1998
INVENTOR(S) : Miyagi et al

It is certified that error appears in the above-identified patent and that said Letters Patent is hereby corrected as shown below:

In Claim 1, delete lines 12-18 and lines 26-48 as they are duplicative of claim elements (d), (e), (f), and (g)--

This certificate supersedes the certificate of correction issued on July 27, 1999

Signed and Sealed this

Fourteenth Day of September, 1999

Attest:

Q. TODD DICKINSON

*Attesting Officer*    *Acting Commissioner of Patents and Trademarks*